(12) United States Patent
Kanemaru

(10) Patent No.: US 9,161,904 B2
(45) Date of Patent: Oct. 20, 2015

(54) AGENT FOR REGENERATING TYMPANIC MEMBRANE OR EXTERNAL AUDITORY CANAL

(75) Inventor: Shin-ichi Kanemaru, Ashiya (JP)

(73) Assignee: Nobelpharma Co., Ltd., Tokyo (JP)

( * ) Notice: Subject to any disclaimer, the term of this patent is extended or adjusted under 35 U.S.C. 154(b) by 0 days.

(21) Appl. No.: 13/001,318

(22) PCT Filed: Jun. 26, 2009

(86) PCT No.: PCT/JP2009/061767
§ 371 (c)(1),
(2), (4) Date: Dec. 23, 2010

(87) PCT Pub. No.: WO2009/157558
PCT Pub. Date: Dec. 30, 2009

(65) Prior Publication Data
US 2011/0110987 A1 May 12, 2011

(30) Foreign Application Priority Data
Jun. 26, 2008 (JP) .................................. 2008-167744

(51) Int. Cl.
| | | |
|---|---|---|
| A61K 9/00 | (2006.01) | |
| A61L 27/20 | (2006.01) | |
| A61L 27/22 | (2006.01) | |
| A61L 27/34 | (2006.01) | |
| A61L 27/54 | (2006.01) | |
| A61L 27/56 | (2006.01) | |
| A61K 38/18 | (2006.01) | |
| A61K 47/42 | (2006.01) | |

(52) U.S. Cl.
CPC ............ *A61K 9/0046* (2013.01); *A61K 38/1825* (2013.01); *A61K 47/42* (2013.01); *A61L 27/20* (2013.01); *A61L 27/222* (2013.01); *A61L 27/225* (2013.01); *A61L 27/34* (2013.01); *A61L 27/54* (2013.01); *A61L 27/56* (2013.01); *A61L 2300/414* (2013.01); *A61L 2430/14* (2013.01)

(58) Field of Classification Search
CPC combination set(s) only.
See application file for complete search history.

(56) References Cited

U.S. PATENT DOCUMENTS

| 6,054,122 A | 4/2000 | MacPhee et al. |
|---|---|---|
| 2005/0229264 A1 | 10/2005 | Chang et al. |
| 2007/0160648 A1 | 7/2007 | Ashton et al. |

FOREIGN PATENT DOCUMENTS

| JP | 10-337302 A | 12/1998 |
|---|---|---|
| JP | 2003-516730 A | 5/2003 |
| JP | 2007-125252 A | 5/2007 |
| RU | 2277423 C1 | 6/2006 |
| RU | 2280459 C2 | 7/2006 |
| WO | WO 00/69449 A2 | 11/2000 |
| WO | WO 2006/007417 A2 | 1/2006 |
| WO | WO 2006/062871 A2 | 6/2006 |
| WO | WO 2006/124021 A1 | 11/2006 |
| WO | WO 2007/005807 A2 | 1/2007 |

OTHER PUBLICATIONS

Rohanizadeh et al., J Mater Sci: Mater Med (2008) 19:1173-1182.*
Japanese Patent Office, International Search Report in International Patent Application No. PCT/JP2009/061767 (Aug. 18, 2009).
Japanese Patent Office, International Written Opinion in International Patent Application No. PCT/JP2009/061767 (Aug. 18, 2009).
Hakuba et al., *The Laryngoscope*, 113: 1352-1355 (2003).
Hakuba et al., *Head and Neck Surgery*, 16(1): 9-13 (2006).
Hakuba et al., *Journal of Otolaryngology of Japan*, 110(4): 261 (2007).
Kazunori et al., *Journal of Otolaryngology of Japan*, 110(4): 299 (2007).
Bahadir et al., *Eur. Arch. Otorhinolaryngol.*, 260: 19-23 (2003).
Goto et at., *Nippon Jibiinkoka Gakkai Kaiho*, 65(6): 723-729 (1962).
Dvorak et al., *Laryngoscope*, 105: 1300-1304 (1995).
Kase et al., *Otolaryngology—Head and Neck Surgery*, 138: 523-527 (2008).
Vrabec et al., *Laryngoscope*, 104:1059-1064 (1994).
European Patent Office, Supplementary European Search Report in European Application No. 09 77 0268 (Oct. 4, 2013).
Chinese Patent Office, Search Report in Chinese Patent Application No. 200980133310.8 (Mar. 14, 2013).
Chongpei et al., "Effect of Basic Fibroblast Growth Factor on Tympanic Membrane Repair," *Journal of Audiology and Speech Pathology*, 15(6): 485-486 (2007).
Fina et al., "Direct Application of Basic Fibroblast Growth Factor Improves Tympanic Membrane Perforation Healing," *Laryngoscope*, 103(7): 804-809 (1993).
Wei et al., "Application of Medical Adhesive Agent in Tympanoplasty," *Central China Medical Journal*, p. 16 (Dec. 31, 1989).
Jie et al., Collection of Dissertations of the Tenth National Otolaryngology—Head and Neck Surgery Academic Conference of the Chinese Medical Association (the second-half volume), p. 847 (2007).

(Continued)

*Primary Examiner* — Michael G Hartley
*Assistant Examiner* — Robert Cabral
(74) *Attorney, Agent, or Firm* — Mintz Levin Cohn Ferris Glovsky and Popeo, P.C.; David G Conlin; Christopher R. Cowles

(57) ABSTRACT

Provided is a tympanic membrane or ear canal regeneration agent comprising a combination of a gelatin sponge that carries basic fibroblast growth factor (bFGF) and a covering material. The covering material is used not only to fix the gelatin sponge to the affected portion, but also for the purpose of preventing drying and infections to provide a culturing environment that is favorable for regenerating tissue isolated from the outside. To promote tissue regeneration, the margin of the tympanic membrane or ear canal defect is preferably freshened in advance.

4 Claims, 2 Drawing Sheets

(56) References Cited

OTHER PUBLICATIONS

Chinese Patent Office, Search Report in Chinese Patent Application No. 200980133310.8 (Jan. 10, 2014).

Pomatilov, Aleksey Alekseevich, "Healing Post-traumatic Defects of the Eardrum by Transplantation of Human Allofibroblastov," University Thesis Dissertation for Medical Sciences Degree (Moscow 1991).

Akita et al., *Wound Repair Regen.*, 12(2): 252-259 (2004) [abstract only].

Kinoshita et al., *Int. J. Oral Maxillofac. Surg.*, 37(3): 275-281 (2008) [abstract only].

* cited by examiner

A.

B.

C.

D.

E.

F.

A.

B.

C.

D.

AGENT FOR REGENERATING TYMPANIC MEMBRANE OR EXTERNAL AUDITORY CANAL

TECHNICAL FIELD

The present invention relates to a tympanic membrane or ear canal regeneration agent comprising a combination of a gelatin sponge that carries basic fibroblast growth factor (bFGF) and a covering material.

BACKGROUND ART

Perforation of the tympanic membrane is a symptom that causes defects such as ruptures and perforations in the tympanic membrane; there are various causes thereof, and in cases of macroscopic dryness in the tympanic cavity without active inflammation, it seems desirable to close the perforation as early as possible. The largest advantage of tympanic membrane closure is an increase in hearing ability. Provided that the inner ear is not disordered, with no special lesions present in the middle ear, an improvement in hearing ability is usually achieved in all cases after tympanic membrane closure, which significantly contributes to an increase in the patient's QOL.

In the presence of a perforation in the tympanic membrane, not only the tympanic membrane is unable to capture adequate sound, but also hearing (listening to words) is further interfered with by the cancelling effect, in which the sound that has directly entered the tympanic cavity goes in the cochlea through the round window and collides with the sound that has entered the cochlea via the normal route. Additionally, the middle ear exposes directly to the ear canal side, which in turn results in weakened resistance to infections and is likely to cause otitis media. A long-persisting infectious state causes sensorineural hearing loss and impaired labyrinthine function due to internal ear hypofunction. For these reasons, it is preferable that the tympanic membrane be closed as much as possible.

For tympanic membrane closure, a variety of therapies are performed according to the size of the perforation, and basically the majority of currently available therapies are surgery-based. Generally, myringoplasty and tympanoplasty are performed. In the former, skin incision in the postauricular part and collection/transplantation of autologous tissue are essential; in the latter, in addition to these procedures, ear canal abrasion is essential. As the perforation of the tympanic membrane increases its size, transplantation of autologous tissue (fascia temporalis) as a substitute for the tympanic membrane becomes more difficult to perform as a surgical technique. Hence, even when surgery is performed, hearing ability is not always be improved. Many sequelae such as postoperative tympanic membrane re-perforation, foreign sensation in the periauricular part, and tinnitus can occur. Furthermore, post-operatively, the tympanic membrane becomes far from the intact tympanic membrane because of latentiation, hypertrophy and the like, and hearing ability decreases. These operations are usually accompanied by hospitalized care for about one day to several weeks, posing drawbacks such as increased mental, physical and economic burdens on the patient.

Likewise, for ear canal soft tissue defects accompanied by bone exposure, surgical treatment has been the only conventional therapy; treatments such as external incision in the postauricular part and collection of autologous tissue have been indispensable.

In recent years, regenerative medicine-oriented methods of tympanic membrane regeneration using a biocompatible scaffold material that carries a growth factor have been proposed (see, for example, Patent Document 1). In particular, some cases of treatment have been reported wherein basic fibroblast growth factor (bFGF) is used as the growth factor, and a sheet-like thin film such as a collagen membrane or a chitin membrane is used as the scaffold material (Non-patent Documents 1 to 3). Also described is a molded product for ear canal reconstruction made of a cylindrical member of bFGF-containing collagen (Patent Document 2).

As another method of regenerating the tympanic membrane that does not rely on surgical operations, a method has been reported in which the perforated portion of the tympanic membrane is covered with the amnion and bonded with fibrin glue (Non-patent Document 2).

However, the efficacy of conventional regenerative medicine-oriented therapies is limited to relatively small tympanic membrane perforations and ear canal defects; these therapies are not applied for tympanic defects larger than a certain size and defects that involve the auditory ossicles because of the inability to repair.

Meanwhile, gelatin sponges are used as a surgical hemostatic, and are also used as a carrier for sustained release of drugs in the treatment of ear diseases (Patent Document 3).

PRIOR ART DOCUMENTS

Patent Documents

Patent Document 1: Pamphlet for International Patent Publication No. 2006/007417
Patent Document 2: JP-A-2007-125252
Patent Document 3: Specification for US Patent Application Publication No. 2007/0160648

Non-Patent Documents

Non-patent Document 1: Hakuba et al., Journal of Otolaryngology of Japan, Vol. 110, No. 4, p. 261, 2007
Non-patent Document 2: Hakuba et al., Head and Neck Surgery, Vol. 16, No. 1, p. 9-13, 2006
Non-patent Document 3: Futai et al., Journal of Otolaryngology of Japan, Vol. 110, No. 4, p. 299, 2007

SUMMARY OF THE INVENTION

Problems to be Solved by the Invention

There is a strong demand for the development of a method of regenerating the tympanic membrane and ear canal based on a regenerative medical technique that makes it possible to repair even large tympanic membrane perforations and ear canal soft tissue defects, for which treatment has traditionally unavoidably relied on surgical operations. Accordingly, it is an object of the present invention to provide a novel tympanic membrane/ear canal regeneration agent capable of repairing defects regardless of the size and position of the defective portion.

Means of Solving the Problems

The present inventor conducted extensive investigations to accomplish the above-described object, and took note of the fact that all conventional techniques are intended to repair defective portions by allowing surrounding tissue to extend along the base of a sheet-like scaffold material bonded to a tympanic membrane perforation or ear canal soft tissue defect. Because it aims to regenerate essentially membranous tissue, the idea of using a sheet-like material as a scaffold seems to be apparently rational. However, provided that the tympanic membrane perforation or ear canal soft tissue defect is localized to a planar portion only, repair would be possible; however, the tympanic membrane is complex in shape and has ossicles adhering thereto, so that it is increasingly difficult to cover the entire surface with a planar sheet-like material as the tympanic defect increases its size. The inability to completely cover the defective portion would make it impossible to repair the tympanic membrane, or would result in adhesion with surrounding tissue, leaving sequelae. The same applies to ear canal soft tissue.

For the reasons above, the present inventor changed the conventional idea of using a sheet-like material, and adopted a gelatin sponge as a scaffold material with a focus on the use of a material that allows the entire defective portion to be covered sterically. Specifically, a gelatin sponge impregnated with bFGF solution was indwelled in a way such that the sponge covered the defective portion of the tympanic membrane or ear canal. Because the gelatin sponge is a material obtained by decomposing collagen, having a larger number of gaps and a higher degree of freedom than collagen, it is characterized in that while functioning as a scaffold for cell growth, it does not interfere with the direction of cell elongation. Accordingly, the gelatin sponge aims to allow regenerating tissue to go into the gelatin sponge and elongate there, rather than to allow the regenerating tissue to elongate along the base of a sheet-like material as conventional.

Furthermore, in this operation, fibrin glue or alginic acid or a salt thereof was applied to the sponge surface, and the sponge was covered and fixed over the defective portion. While a technique is known in which a base material for tissue regeneration is fixed to surrounding tissue using a bioadhesive material, the present inventor covered the sponge surface with a covering material, not merely as an adhesive agent, but for the purpose of insulating the regenerating portion from the outside to create an environment suitable for in vivo culture. From the same viewpoint, when the margin of tympanic membrane perforations and ear canal soft tissue defects was old, it was freshened using a surgical knife or a protein denaturant and the like.

As a result, even for tympanic membrane perforations with a defect involving more than ⅔ of the membrane and ear canal soft tissue defects exceeding 2 cm in wound diameter, for which conventional methods are not applied, closure of the defect and an improvement in hearing ability were noted in all cases, with no sequelae observed.

From the above, the present inventor confirmed that by using a bFGF-carrying gelatin sponge and a covering material in combination, it is possible to regenerate the tympanic membrane and ear canal inexpensively, conveniently, and safely, even for patients with a severe tympanic membrane perforation or ear canal soft tissue defect, for which treatment has conventionally unavoidably relied on surgical operations, and have developed the present invention.

Accordingly, the present invention is as described below:

[1] A tympanic membrane or ear canal regeneration agent comprising a combination of a gelatin sponge that carries basic fibroblast growth factor and a covering material.

[2] The agent described in [1], wherein the covering material is fibrin glue or a water-soluble polymeric polysaccharide or a derivative thereof.

[3] The agent described in [2], wherein the water-soluble polymeric polysaccharide is chitin, chitosan or alginic acid or a salt thereof.

[4] The agent described in any one of [1] to [3], wherein the margin of a tympanic membrane perforation or ear canal soft tissue defect has been freshened.

[5] A method of regenerating the tympanic membrane or ear canal, comprising indwelling a gelatin sponge that carries a therapeutically effective amount of basic fibroblast growth factor in a tympanic membrane perforation or ear canal soft tissue defective portion in a patient with a tympanic membrane perforation or ear canal soft tissue defect, and covering the sponge with a covering material.

[6] The method of regeneration described in [5], wherein the covering material is fibrin glue or a water-soluble polymeric polysaccharide or a derivative thereof.

[7] The method of regeneration described in [6], wherein the water-soluble polymeric polysaccharide is chitin, chitosan or alginic acid or a salt thereof.

[8] The method of regeneration described in any one of [5] to [7], wherein the margin of the tympanic membrane perforation or ear canal soft tissue defect is freshened in advance.

[9] A use of a covering material and basic fibroblast growth factor carried by a gelatin sponge for producing a tympanic membrane or ear canal regeneration agent.

[10] The use described in [9], wherein the covering material is fibrin glue or a water-soluble polymeric polysaccharide or a derivative thereof.

[11] The use described in [10], wherein the water-soluble polymeric polysaccharide is chitin, chitosan or alginic acid or a salt thereof.

[12] The use described in any one of [9] to [11], wherein the margin of the tympanic membrane perforation or ear canal soft tissue defect has been freshened.

Effect of the Invention

By using a gelatin sponge as a scaffold material, it is possible to sterically cover the entire defective portion of the tympanic membrane or the ear canal to achieve complete coverage of the defective portion. Additionally, tympanic membrane tissue regenerates itself while advancing in the gelatin sponge. Therefore, according to the present invention, repair of the tympanic membrane or the ear canal is possible even in cases of large or complex defects.

Covering the gelatin sponge surface with a covering material prevents drying and infections, making it possible to create a good culturing environment isolated from the outside.

Furthermore, the gelatin sponge undergoes hydrolysis and disappears in vivo within 1 month, working in favor of the regeneration of the tympanic membrane and ear canal soft tissue.

MODE FOR EMBODYING THE INVENTION

Figure 1:
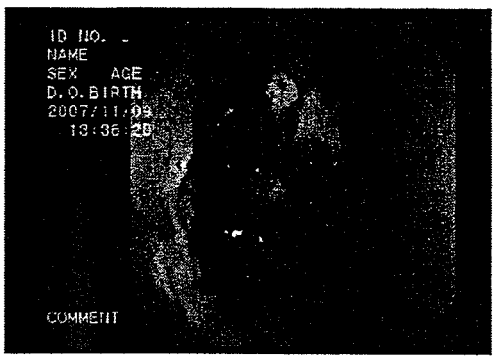
FIG. 1 A drawing showing an example treatment for regenerating the tympanic membrane using the tympanic membrane regeneration agent of the present invention. A. A large perforation involving about ⅔ of the tympanic membrane is noted. B. The margin of the tympanic membrane perforation is bruised using a tympanic membrane incisional knife to form a fresh wound around. C. A bFGF-carrying gelatin sponge is indwelled in the perforated portion and fixed with fibrin glue. D. At 3 weeks after treatment, the tympanic membrane perforation is completely closed by epithelium. E. At 6 weeks after treatment, the epithelium thins slightly, becoming more like the tympanic membrane. F. At 12 weeks after treatment, the epithelium becomes still more like the normal tympanic membrane.
Figure 1:
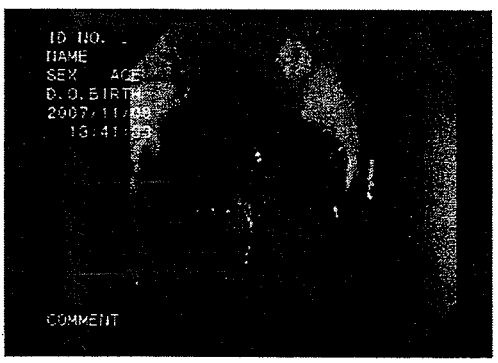
Figure 1:
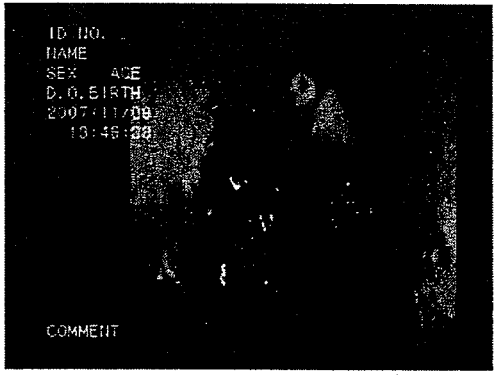
Figure 1:
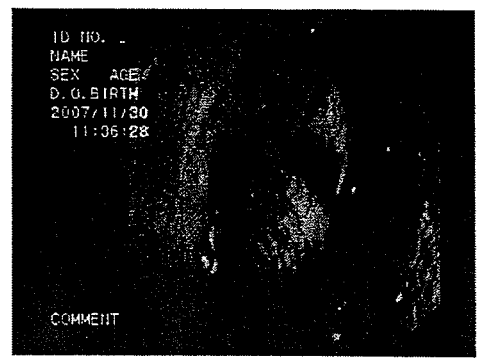
Figure 1:
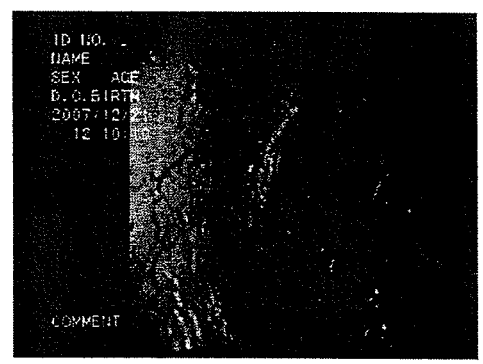
Figure 1:
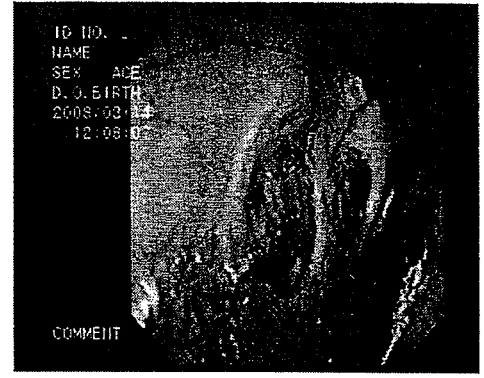

The growth factor bFGF used in the tympanic membrane/ear canal regeneration agent of the present invention has a direct proliferating effect on cells and neovascularization ability. The tympanic membrane has a 3-layer structure; to ensure that the essential sound conduction function is exhibited to the fullest, it is important to maintain this 3-layer structure. However, cases of breakage and spontaneous cure of the tympanic membrane are often encountered wherein the tympanic membrane is thin with only the epithelial layer regenerated while the 3-layer structure is not maintained.

For the regeneration thereof, proliferation of fibroblasts as a scaffold and maintenance of a bloodstream sufficient to support the 3-layer structure are indispensable. From this viewpoint, bFGF has ideal features. Specifically, as indicated by the designation thereof, bFGF has the direct action of stimulating fibroblast proliferation, and also has the action of inducing blood vessels and supplying nutrients to surrounding tissue.

As the bFGF in the present invention, a homologue thereof may be used. The bFGF in the present invention and/or a homologue thereof is obtained as a natural product, or by isolated and purified using a microorganism or cultured cells by gene recombination technology, or by chemically modifying or biologically modifying the same. As the bFGF used in the present invention, human bFGF or a homologue thereof is particularly preferable.

A homologue of bFGF means the polypeptide [I] or [II] below.

[I] A polypeptide consisting of substantially the same amino acid sequence as a bFGF produced in a mammal. Here, "substantially the same amino acid sequence" means an amino acid sequence that has 1 to 6 amino acids substituted by other kinds of amino acids, and that possesses the bioactivity of bFGF. [II] A polypeptide wherein a supplementary amino acid segment is added to the N-terminus and/or C-terminus of a bFGF produced in a mammal, or to the N-terminus and/or C-terminus of the polypeptide [I] above. A supplementary amino acid segment means one that consists of 1 to 12 amino acids, and that does not affect the biological activity of the bFGF or the biological activity of the polypeptide [I] above.

Human bFGF is a polypeptide of 146 amino acids; in the preparation of the present invention, as a homologue of human bFGF (the aforementioned homologue [I]), for example, the polypeptide of 146 amino acids described in National Publication of International Patent Application No. JP-2-504468 may be used. This polypeptide is one wherein each of the 69-position cysteine (Cys.) and the 87-position cysteine (Cys) that constitute the amino acid sequence of human bFGF is substituted by serine (Ser).

As the aforementioned homologue [II], for example, the polypeptide of 155 amino acids described in National Publication of International Patent Application No. JP-63-500843 may be used. This polypeptide is one wherein a segment of 9 amino acids is added to the N-terminus of human bFGF.

Also, a polypeptide of 147 amino acids with Met-added to the N-terminus, and the polypeptide of 157 amino acids with a segment consisting of 11 amino acids added to the N-terminus, described in National Publication of International Patent Application No. JP-63-501953, may be used.

A particularly preferable bFGF is trafermin (genetical recombination).

In the preparation of the present invention, one kind of bFGF may be used alone, or a plurality of kinds may be used in combination. Furthermore, as stated above, a plurality of homologues of bFGF exist, and these homologues may be used alone or used in combination.

Because the abundance of bFGF in a living organism is extremely low, it is particularly preferable for commercially stably supplying the preparation of the present invention that bFGF, or a homologue thereof, produced using a microorganism such as *Escherichia coli* or cultured cells by gene recombination technology be used. When a gene for producing bFGF or a homologue thereof (in this case, generally the aforementioned polypeptide (I)) is inserted into a microorganism or cultured cells, the product from this microorganism or cultured cells is generally one with a supplementary amino acid segment added to the N-terminus and/or C-terminus of bFGF, or to the N-terminus and/or C-terminus of the polypeptide [I] above, i.e., the aforementioned polypeptide [II].

The choice of gelatin that serves as a raw material for the gelatin sponge in the present invention is not particularly limited; any commonly available one can be used. For example, a crude collagen obtained by treating a bone, ligament, tendon, or skin of a bovine, pig, chicken, salmon or the like with an acid or alkali, thermally extracted with water, and the like can be mentioned. Not only one kind of gelatin, but also gelatins with different materials and different physical properties such as solubility, molecular weight, and isoelectric point may be used in appropriate blends.

The gelatin sponge used in the present invention may have been crosslinked to increase its water resistance, so as to allow it to serve as a scaffold for regenerating tissue for a period sufficient to close the defect in the tympanic membrane or ear canal, as far as it does not lose a softness that enables complete coverage of the morphologically complex margin of tympanic membrane perforation and the margin of ear canal defect. The method of crosslinking is not particularly limited; examples include a method involving the use of a crosslinking agent, vacuum thermal dehydration, dry heating, γ-ray irradiation, ultraviolet ray irradiation, electron ray irradiation, X-ray irradiation and the like.

The gelatin sponge of the present invention has a large number of fine pores, and offers a higher degree of freedom than collagen. By having the large number of fine pores, the gelatin sponge, when used as a scaffold material, allows surrounding cells to enter the sponge easily, making it possible to regenerate the tympanic membrane and ear canal in a good way. This is a distinct difference from conventional regeneration agents prepared using a sheet-like scaffold material. Specifically, for scaffolds like a sheet-like collagen membrane, the tissue does not regenerate itself while advancing in the scaffold, but does regenerate itself either upwardly or downwardly. This does not enable the complete covering of the defective portion of a tympanic membrane defect larger than a certain size, so that repair of the tympanic membrane is impossible, or adhesion to surrounding tissue occurs and sequelae are left.

In view of the fact that cells readily enter the sponge to ensure good cell adhesion, it is preferable that the mean pore diameter of the fine pores of the gelatin sponge of the present invention be about 10 μm or more, and it is preferable that to prevent a reduction in the tympanic membrane or ear canal regeneration rate due to low cell density, the mean diameter be about 500 μm or less. A more preferable range is about 100 to about 400 μm.

The gelatin sponge of the present invention may contain another bioabsorbable polymeric material, as far as the function thereof is not adversely influenced. Such bioabsorbable polymeric materials include, for example, synthetic polymers such as polylactic acid, polyglycolic acid, poly-ε-caprolactone, lactic acid-glycolic acid copolymer, glycolic acid-ε-caprolactone copolymer, lactic acid-ε-caprolactone copolymer, polycitric acid, polymalic acid, poly-α-cyanoacrylate, poly-β-hydroxy acid, polytrimethylene oxalate, polytetramethylene oxalate, poly-ortho-esters, poly-ortho-carbonates, polyethylene carbonate, poly-γ-benzyl-L-glutamate, poly-γ-methyl-L-glutamate, and poly-L-alanine; natural polymers such as polysaccharides such as starch, alginic acid, hyaluronic acid, chitin, pectic acid and derivatives thereof, and proteins such as gelatin, collagen, albumin, and fibrin, and the like.

The gelatin sponge of the present invention can be produced by, for example, stirring and foaming an aqueous solution of gelatin using a homogenizer at a rotation rate of about 3000 to about 10000 rpm for about 10 seconds to about 5 minutes, then casting the aqueous solution of gelatin into a mold of an appropriate size, and frozen at about −40 to about −80° C. for about 30 to about 120 minutes, thereafter freeze-drying this frozen matter under conditions of, for example, about 0.1 Torr. If the concentration of the aqueous solution of gelatin is too high, the softness of the gelatin sponge obtained decreases, so that it is preferable that the concentration be adjusted to, for example, about 3 w/w % or less. If further crosslinking is necessary, crosslinking can be performed as appropriate.

As the gelatin sponge of the present invention, a commercially available hemostatic (for example, Spongel (registered trademark) (Astellas Pharma), Gelfoam (registered trademark) (Pharmacia & Upjohn) and the like) can be used.

The shape and size of the gelatin sponge of the present invention are not particularly limited, as far as it is sufficiently large to cover the defective portion of the patient's tympanic membrane or ear canal.

The method of allowing bFGF to be carried by the gelatin sponge thus prepared is not particularly limited; for example, an aqueous solution of bFGF may be added drop by drop to the gelatin sponge, or the gelatin sponge may be swollen by the addition to an aqueous solution of bFGF.

The amount of bFGF to be carried by the gelatin sponge is not particularly limited, as far as it is an amount sufficient to regenerate the tympanic membrane or ear canal; it is, for example, about 0.1 to about 1000 μg, preferably about 1 to about 100 μg, per administration site.

The bFGF-carrying gelatin sponge preparation thus obtained can also be freeze-dried. If desired, freeze-drying is performed by, for example, freezing the preparation in liquid nitrogen for 30 minutes or more or at −80° C. for 1 hour or more, and then drying the preparation using a freeze-drying machine for 1 to 3 days.

The tympanic membrane/ear canal regeneration agent of the present invention is applicable in all cases, as far as the patient's tympanic membrane perforation or ear canal soft tissue defect is not accompanied by active infections/inflammation in the middle ear/external ear. For example, cases of tympanic membrane perforation include chronic otitis media, re-perforation after tympanic membrane closure surgery or tympanoplasty, old traumatic tympanic membrane perforation, perforation remaining after tympanic membrane incision or tympanic membrane tube indwelling for otitis media with effusion and the like. Example cases of ear canal soft tissue defect include those with an ear canal soft tissue defect and ear canal bone exposure after ear canal cholesteatoma resection, tympanoplasty or ear canal tumor resection.

The tympanic membrane/ear canal regeneration agent of the present invention can preferably be used particularly for patients with a large tympanic membrane perforation or ear canal soft tissue defect for which therapies using a conventional regenerative medical technique are not indicated. Specifically, in patients with a tympanic membrane perforation wherein more than ⅓, particularly more than ⅔, of the tympanic membrane is defective, repair of the tympanic membrane is possible. In patients having an ear canal soft tissue defect having a maximum diameter of 1 cm or more, particularly 2 cm or more, repair of the ear canal is possible.

The bFGF-carrying gelatin sponge is adjusted to a size larger than the defective portion of the tympanic membrane or ear canal, and is indwelled in a way such that the entire defective portion is covered. Here, in case of an old margin of the defective portion, it is desirable that the margin be freshened to promote tissue regeneration. Methods of freshening include, for example, a method wherein the epithelium of the margin is removed by bruising the margin using a surgical knife or the like, or by a treatment with a drug having a protein-denaturing effect, such as aluminum acetate or a high concentration of a local anesthetic.

This drug-based method is particularly effective in cases where the ear canal is so narrow in shape that the margin of the tympanic membrane perforation is difficult to freshen; first, a gelatin sponge containing aluminum acetate is indwelled in the defective portion, and, about 30 minutes later, it is removed. Thereafter, anesthesia with 4% lidocaine hydrochloride is performed, after which the denatured tissue of the margin (discolored to white) is removed to the maximum possible extent, whereby freshening can be achieved.

A further feature of the present invention resides in the fact that the surface of the bFGF-carrying gelatin sponge indwelled in the defect is covered with a covering material. As the covering material used in the present invention, any biocompatible material can be used, as far as it has adhesiveness sufficient to keep the bFGF-carrying gelatin sponge fixed on the defective portion of the tympanic membrane or ear canal, and is capable of providing the surface and inside of the sponge with a culturing environment suitable for the cells of regenerated tissue by being isolated from the external environment; examples include fibrin glue (blood fibrinogen and thrombin extracts; commercially available as Bolheal (registered trademark) (Astellas Pharma), TISSEEL (registered trademark) (Baxter), or Beriplast (registered trademark) (CSL Behring)), alginic acid or a salt thereof (for example, calcium alginate, sodium alginate), and water-soluble polymeric polysaccharides such as chitin and chitosan.

As a method of preparing an alginic acid salt (calcium alginate), and shaping it into a membrane foam, for example, 3.3 ml of a 2% aqueous solution of sodium alginate is uniformly casted in a way such that the entire base of a Petri dish of 10-ml capacity comes into contact with this aqueous solution. Subsequently, 5 ml of a 3% aqueous solution of calcium chloride is uniformly spread over the same Petri dish to allow the aqueous solution of sodium alginate and the aqueous solution of calcium chloride to come into contact with each other sufficiently, after which several minutes are waited. After the remaining liquid is removed, the dish is washed with distilled water and allowed to dry spontaneously, whereby a calcium alginate membrane is prepared. After drying, the membrane is separated, shaped into an appropriate size, and sterilized with EO gas, whereby the alginic acid salt can be prepared as a covering material.

When the covering material is liquid, it can be administered by dripping several drops thereof on the surface of the bFGF-carrying gelatin sponge indwelled in the defective portion, or by spraying it using a sprayer known per se, and the like. When the covering material is a sheet-like substance, it can be placed in a way such that the surface of the bFGF-carrying gelatin sponge indwelled in the defective portion is covered.

The present invention is hereinafter described more specifically by means of the following Examples, which, however, do not limit the present invention in any way.

EXAMPLES

Example 1

Regeneration of Tympanic Membrane

1) Patient Selection

The study subjects comprised various patients who were confirmed to have a tympanic membrane perforation, and not to have an active infection or inflammation in the middle ear/external ear, including cases of chronic otitis media (n=9), cases of re-perforation after tympanic membrane closure surgery or tympanoplasty (n=7), cases of old traumatic perforation of the tympanic membrane (n=5), cases of perforations remaining after tympanic membrane incision or tympanic membrane tube indwelling for otitis media with effusion (n=10) and the like. The size of tympanic membrane perforation did not matter.

The patients were divided into three groups according to the size of tympanic membrane perforation. Specifically, patients having a tympanic membrane perforation involving less than $1/3$, $1/3$ to $2/3$, and more than $2/3$ of the entire tympanic membrane were classified under Grade I, II, and III, respectively.

2) Method of Treatment and Follow-Up Examination

After confirming the presence of a tympanic membrane perforation and the absence of active infections and inflammation, cotton soaked with 4% lidocaine hydrochloride was inserted in the ear canal in a way such that it came in contact with the perforated portion of the tympanic membrane. About 15 minutes later, under a microscope, the margin of the tympanic membrane perforation was bruised using a tympanic membrane incisional knife or the like, and the epithelium of the margin of the perforation was removed around (FIG. 1B). Subsequently, a gelatin sponge (Spongel (registered trademark): Astellas) mass larger than the tympanic membrane perforation was impregnated with bFGF (Fiblast (registered trademark): Kaken Pharmaceutical), and the bFGF-carrying gelatin sponge mass was indwelled in a way such that the perforated portion of the tympanic membrane was fully covered (FIG. 1C). Thereafter, this was fixed with several drops of fibrin glue (Beriplast (registered trademark): CSL Behring).

After the treatment, the patients were instructed not to do anything that exerts pressure on their ears, such as vigorous nasal sucking and nose blowing, and not to allow water to enter their ears during hair washing and bathing.

A checkup after 3 weeks revealed firm adhesion of the covering material and gelatin sponge remaining on the surface; when this was carefully removed using a Rosen probe and the like, a regenerated tympanic membrane was noted thereunder (FIG. 1D). In cases where the perforation was not closed by a single treatment, the same treatment was repeated.

At that time, the regenerated tympanic membrane occurred as a thickened, vessel-rich tissue, but it thinned with the elapse of time (FIG. 1E), and became undistinguishable from the normal tympanic membrane in about 2 months (FIG. 1F).

3) Results

Tympanic membrane regenerative treatment was performed by this method on 31 ears in 26 subjects. The results are shown in Table 1. The results were summarized by perforation size (Grade I to III) in terms of the number of treatments required to achieve closure, closure rate, degree of hearing ability improvement, treatment time excluding anesthesia time, and the presence or absence of sequelae. The results from five patients in whom a gelatin sponge impregnated with physiological saline alone without using bFGF was indwelled in a perforated portion of the tympanic membrane are shown in Table 2.

TABLE 1

| | Classification by size of tympanic membrane perforation | | |
| --- | --- | --- | --- |
| | Grade I (n = 3) | Grade II (n = 15) | Grade III (n = 13) |
| Number of treatments (Mean) | 1 (1.0) | 1-3 (1.6) | 1-4 (1.8) |
| Closure rate | 100% | 100% | 100% |
| Degree of hearing ability improvement (3-fraction method) | 15.8 dB | 23.3 dB | 28.5 dB |
| Treatment time excluding anesthesia time | 8 minutes 50 seconds | 9 minutes 20 seconds | 11 minutes 40 seconds |
| Sequelae | None | None (transient otorrhea n = 2, tympanic recess n = 1) | None (transient otorrhea n = 3, tympanic recess n = 1) |

Grade I: perforation less than $1/3$
Grade II: perforation $1/3$-$2/3$
Grade III: perforation more than $2/3$

TABLE 2

| | Classification by size of tympanic membrane perforation | | |
| --- | --- | --- | --- |
| | Grade I (n = 0) | Grade II (n = 3) | Grade III (n = 2) |
| Number of treatments | | 4 times | 4 times |
| Closure rate | | 0% | 0% |

Even in case of the gelatin sponge impregnated with physiological saline alone without using bFGF, a slight tendency toward closure of the tympanic membrane was noted. This shows that regeneration of the tympanic membrane is promoted even by indwelling a scaffold alone; closure seems to be possible for very small tympanic membrane perforations;

however, when the tympanic membrane perforation was large, it could not be closed even when the number of treatments was increased.

Meanwhile, when bFGF was added, the tympanic membrane perforation closed in all cases, irrespective of the size of tympanic membrane perforation. This shows that cell regeneration is subject to limitations with the use of a scaffold alone; it is thought that in cases of tympanic membrane perforations that are larger than a certain size, addition of a growth factor such as bFGF seems to be necessary and indispensable. Regarding the degree of hearing ability improvement, a normal level was restored, irrespective of the size of tympanic membrane perforation; regeneration of a functionally normalized tympanic membrane was observed.

Example 2

Regeneration of Ear Canal Soft Tissue

1) Patient Selection

The study subjects comprised patients after ear canal cholesteatoma resection (n=7), patients after tympanoplasty (n=2), and a patient after ear canal tumor resection (n=1), all of whom experienced a defect of ear canal soft tissue and exposure of ear canal bone. The size of the defect did not matter.

2) Method of Treatment and Follow-Up Examination

Figure 2:
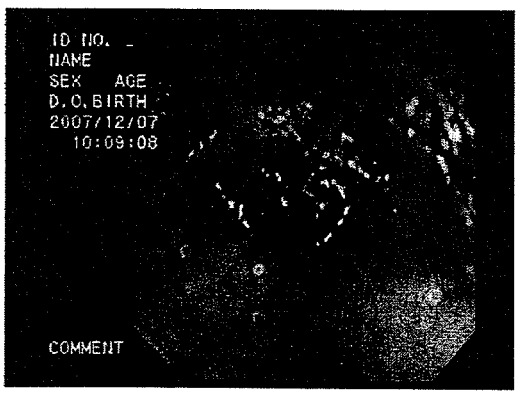
FIG. 2 A drawing showing an example treatment for regenerating the ear canal using the ear canal regeneration agent of the present invention. A. A soft tissue defect and bone exposure are noted in a wound with cholesteatoma removed therefrom. B. A gelatin sponge mass is impregnated with bFGF, and the bFGF gelatin sponge mass is indwelled in a way such that the wound is fully covered. C. The sponge mass is fixed with alginic acid or a salt thereof (or fibrin glue). D. At 2 weeks after treatment, the alginic acid or salt thereof and the like remaining on the surface are removed; it is confirmed that the wound has been completely closed, and that regeneration has been achieved in nearly the same state as normal tissue.
Figure 2:
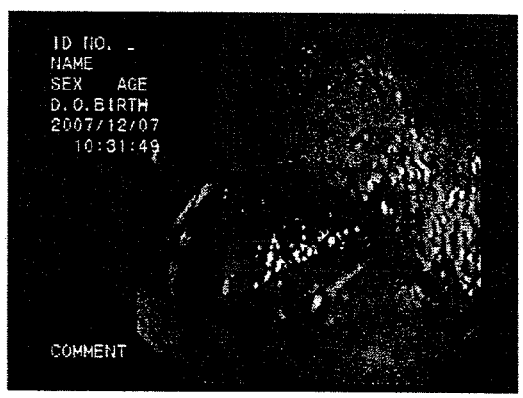
Figure 2:
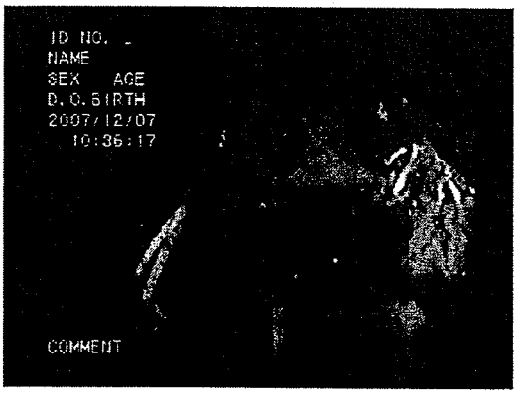
Figure 2:
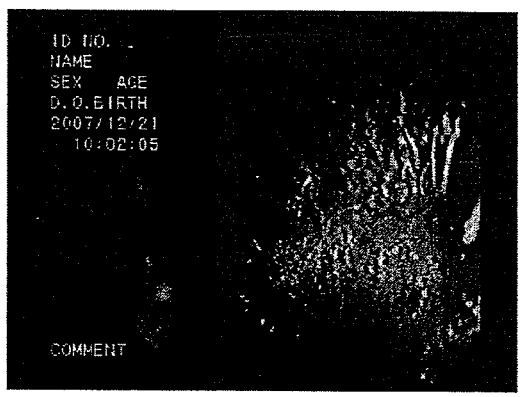

After verifying the absence of active infections/inflammation in the wound, local anesthesia was performed. Under a microscope, the cholesteatoma and tumor were resected from inside of the ear canal for patients with ear canal cholesteatoma or an ear canal tumor, and a fresh wound was made using a surgical knife or the like for patients with ear canal bone exposure following tympanoplasty, after which a gelatin sponge mass larger than the wound was impregnated with bFGF, and the bFGF-carrying gelatin sponge mass was indwelled in a way such that it fully covered the defective portion (FIG. 2B). Thereafter, this was covered with several drops of fibrin glue or a calcium alginate membrane (FIG. 2C).

The patients were instructed to refrain from picking their ears, and not to allow water to enter their ear canals during bathing, hair washing and face washing.

Checkups after 2 or 3 weeks revealed firm adhesion of the covering material and gelatin sponge remaining on the surface; when this was carefully removed using a Rosen probe and the like, completely regenerated ear canal epithelium and soft tissue were noted thereunder (FIG. 2D). If the regeneration was inadequate by a single treatment, the same treatment was repeated.

3) Results

Ear canal regenerative treatment was performed by this method on 10 patients. The results are shown in Table 3. The results were summarized by size of defect (Grade I to III) in terms of the number of treatments required to achieve closure, closure rate, treatment time excluding anesthesia time, and the presence or absence of sequelae.

TABLE 3

| | Classification by wound size | | |
|---|---|---|---|
| | Grade I (n = 6) | Grade II (n = 3) | Grade III (n = 1) |
| Number of treatments (Mean) | 1-2 (1.3) | 1-3 (2.0) | 1 (1.0) |
| Closure rate | 100% | 100% | 100% |
| Treatment time excluding anesthesia time | 7 minutes 30 seconds | 8 minutes 40 seconds | 15 minutes 10 seconds |
| Sequelae | None | None | None |

Grade I: Maximum diameter of wound <1.0 cm
Grade II: 1.0-2.0 cm
Grade III: >2.0 cm

INDUSTRIAL APPLICABILITY

According to the present invention, tympanic membrane perforations and ear canal soft tissue defects can be merely treated on an outpatient basis for about 10 minutes, without being accompanied by a full surgical treatment, so that the need for hospitalization and frequent hospital visits is obviated. Because regeneration of the tympanic membrane/ear canal is possible irrespective of the size and cause of the defect, the present invention is applicable to patients for whom treatment by conventional regeneration medical techniques is not indicated. Furthermore, the surgical technique involved is simple, repeated treatment does not produce sequelae, and regeneration of a fully normal tympanic membrane/ear canal is possible. Additionally, hearing ability is normalized just after the treatment, causing no hindrance to daily activities. Therefore, the mental, physical, temporal, and economic burdens on the patient are lessened, so that the present invention is highly favorable from a medical economic viewpoint.

This application is based on a patent application No. 2008-167744 filed in Japan (filing date: Jun. 26, 2008), the contents of which are incorporated in full herein.

The invention claimed is:

1. A method of regenerating the tympanic membrane or ear canal, comprising indwelling a gelatin sponge that carries a therapeutically effective amount of basic fibroblast growth factor in a tympanic membrane perforation or ear canal soft tissue defective portion in a patient with a tympanic membrane perforation or ear canal soft tissue defect, and covering the sponge with fibrin glue as a covering material.

2. The method of regeneration according to claim 1, wherein a margin of the tympanic membrane perforation or ear canal soft tissue defect is freshened in advance.

3. The method according to claim 1, wherein the amount of basic fibroblast growth factor to be carried by the gelatin sponge is about 0.1 to about 1000 μg per administration site.

4. The method according to claim 1, wherein the mean pore diameter of the fine pores of the gelation sponge is about 100 to about 400 μm.

* * * * *